(12) United States Patent
Thompson

(10) Patent No.: US 12,281,325 B1
(45) Date of Patent: Apr. 22, 2025

(54) COMPOSITION FOR REGULATING PRODUCTION OF PROTEINS

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/784,317

(22) Filed: Jul. 25, 2024

(51) Int. Cl.
*C12N 15/86* (2006.01)
*C07K 14/47* (2006.01)

(52) U.S. Cl.
CPC .......... *C12N 15/86* (2013.01); *C07K 14/4746* (2013.01); *C12N 2750/14143* (2013.01)

(58) Field of Classification Search
CPC .......... C12N 15/86; C12N 2750/14143; C07K 14/4746
See application file for complete search history.

(56) References Cited

U.S. PATENT DOCUMENTS 11,530,423 B1 * 12/2022 Thompson ............. C12N 15/86

FOREIGN PATENT DOCUMENTS

WO WO-2013151666 A2 * 10/2013 ............. A61K 38/17

OTHER PUBLICATIONS

Zhang et al. "Algorithm for optimized mRNA design improves stability and immunogenicity." Nature 621.7978 (2023): 396-403 (Year: 2023).*

* cited by examiner

*Primary Examiner* — Jeremy C Flinders
*Assistant Examiner* — Alexander W Nicol
(74) *Attorney, Agent, or Firm* — Gowling WLG (Canada) LLP

(57) ABSTRACT

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a protein, such as p53.

7 Claims, No Drawings

Specification includes a Sequence Listing.

COMPOSITION FOR REGULATING PRODUCTION OF PROTEINS

This application contains a Sequence Listing electronically submitted via Patent Center to the United States Patent and Trademark Office as an XML Document file entitled "A8149594US-Sequence Listing ST26.xml" created on 2024 Jul. 23 and having a size of 15,984 bytes. The information contained in the Sequence Listing is incorporated by reference herein.

TECHNICAL FIELD

The present disclosure generally relates to compositions for regulating the production of proteins. In particular, the present disclosure relates to compositions for regulating gene expression and consequently, the production, of proteins.

BACKGROUND

Bioactive molecules, including tumour suppressor proteins, are necessary for the homeostatic control of biological systems.

When bioactive molecules are over-expressed, under-expressed or mis-expressed, homeostasis is lost, and disease is often the result.

As such, it may be desirable to establish therapies, treatments and/or interventions that address the losses of homeostasis and the regulation of bioactive molecules in order to prevent or treat the resulting disease.

SUMMARY

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a protein, such as the tumour suppressor protein, p53

In some embodiments of the present disclosure the compositions comprise a plasmid of deoxyribonucleic acid (DNA) that includes one or more insert sequences of nucleotides that encode for the production of mRNA and a backbone sequence of nucleotides that facilitates introduction of the one or more insert sequences into one or more of a subject's cells where it is expressed and/or replicated. Expression of the one or more insert sequences by one or more cells of the subject results in an increased production of the mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding an mRNA sequence that encodes for the protein p53.

Some embodiments of the present disclosure relate to a method of making a composition/target cell complex. The method comprising a step of administering an RP comprising SEQ ID NO. 1 and SEQ ID NO. 2 to a target cell for forming the composition/target cell complex, wherein the composition/target cell complex causes the target cell to increase production of one or more sequences of mRNA that increases production of a target biomolecule.

Embodiments of the present disclosure relate to at least one approach for inducing endogenous production of one or more sequences of mRNA that encodes for a target biomolecule, for example p53. A first approach utilizes gene vectors containing nucleotide sequences for increasing the endogenous production of one or more sequences of mRNA, which are complete or partial sequences and/or combinations thereof of p53, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein molecule that is found within a subject. A biomolecule may be endogenous or exogenous to a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of mRNA that increases the production of target biomolecules, such as a protein.

In some embodiments of the present disclosure, the target biomolecule is p53.

Some embodiments of the present disclosure relate to a composition that can be administered to a subject with a condition that results, directly or indirectly, from the dysregulated production of a biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both of one or more sequences of mRNA that each encode for one or more biomolecules.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for one or more biomolecules, such as p53.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ TCID$_{50}$/kg (50% tissue culture infective dose per kilogram of the patient's body mass). In some embodiments of the present disclosure, the therapeutically effective amount of the composition that is administered to the patient is about $1 \times 10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1 \times 10^{16}$ TCP/kg.

Some embodiments of the present disclosure relate to an adeno-associated virus (AAV) genome consisting of an RP that when operable inside a target cell will cause the target cell to produce a mRNA sequence that upregulates production of a biomolecule, with an example being p53. The RP is comprised of AAV2 inverted terminal repeats (ITRs), a composite CASI promoter, and a human growth hormone (HGH) signal peptide followed by a mRNA expression cassette encoding for p53, followed by a Woodchuck Hepatitis Virus post-transcriptional regulatory element (WPRE) and a Simian virus 40 (SV40) polyadenylation (polyA) signal.

```
SEQ ID NO. 1 (backbone sequence No. 1):
5' TCTAGAAAGATCTAACTTGTTTATTGCAGCTTATAATGGTTACAAATAAAGCAATAG

CATCACAAATTTCACAAATAAAGCATTTTTTTCACTGCATTCTAGTTGTGGTTTGTCC

AAACTCATCAATGTATCTTATCATGTCTGGATCTCGACCTCGACTAGAGCATGGCTA

CGTAGATAAGTAGCATGGCGGGTTAATCATTAACTACAAGGAACCCCTAGTGATGG

AGTTGGCCACTCCCTCTCTGCGCGCTCGCTCGCTCACTGAGGCCGGGCGACCAAAGG

TCGCCCGACGCCCGGGCTTTGCCCGGGCGGCCTCAGTGAGCGAGCGAGCGCGCAGC

TGGCGTAATAGCGAAGAGGCCCGCACCGATCGCCCTTCCCAACAGTTGCGCAGCCT

GAATGGCGAATGGCGATTCCGTTGCAATGGCTGGCGGTAATATTGTTCTGGATATTA

CCAGCAAGGCCGATAGTTTGAGTTCTTCTACTCAGGCAAGTGATGTTATTACTAATC

AAAGAAGTATTGCGACAACGGTTAATTTGCGTGATGGACAGACTCTTTTACTCGGTG

GCCTCACTGATTATAAAAACACTTCTCAGGATTCTGGCGTACCGTTCCTGTCTAAAA

TCCCTTTAATCGGCCTCCTGTTTAGCTCCCGCTCTGATTCTAACGAGGAAAGCACGTT

ATACGTGCTCGTCAAAGCAACCATAGTACGCGCCCTGTAGCGGCGCATTAAGCGCG

GCGGGTGTGGTGGTTACGCGCAGCGTGACCGCTACACTTGCCAGCGCCCTAGCGCCC

GCTCCTTTCGCTTTCTTCCCTTCCTTTCTCGCCACGTTCGCCGGCTTTCCCCGTCAAGC

TCTAAATCGGGGGCTCCCTTTAGGGTTCCGATTTAGTGCTTTACGGCACCTCGACCCC

AAAAAACTTGATTAGGGTGATGGTTCACGTAGTGGGCCATCGCCCTGATAGACGGTT

TTTCGCCCTTTGACGTTGGAGTCCACGTTCTTTAATAGTGGACTCTTGTTCCAAACTG

GAACAACACTCAACCCTATCTCGGTCTATTCTTTTGATTTATAAGGGATTTTGCCGAT

TTCGGCCTATTGGTTAAAAAATGAGCTGATTTAACAAAAATTTAACGCGAATTTTAA

CAAAATATTAACGTTTACAATTTAAATATTTGCTTATACAATCTTCCTGTTTTTGGGG

CTTTTCTGATTATCAACCGGGGTACATATGATTGACATGCTAGTTTTACGATTACCGT

TCATCGATTCTCTTGTTTGCTCCAGACTCTCAGGCAATGACCTGATAGCCTTTGTAGA

GACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTAC

CTACACATTACTCAGGCATTGCATTTAAAATATATGAGGGTTCTAAAAATTTTTATCC

TTGCGTTGAAATAAAGGCTTCTCCCGCAAAAGTATTACAGGGTCATAATGTTTTTGG

TACAACCGATTTAGCTTTATGCTCTGAGGCTTTATTGCTTAATTTTGCTAATTCTTTGC

CTTGCCTGTATGATTTATTGGATGTTGGAATTCCTGATGCGGTATTTTCTCCTTACGC
```

-continued

```
ATCTGTGCGGTATTTCACACCGCATATGGTGCACTCTCAGTACAATCTGCTCTGATGC

CGCATAGTTAAGCCAGCCCCGACACCCGCCAACACCCGCTGACGCGCCCTGACGGG

CTTGTCTGCTCCCGGCATCCGCTTACAGACAAGCTGTGACCGTCTCCGGGAGCTGCA

TGTGTCAGAGGTTTTCACCGTCATCACCGAAACGCGCGAGACGAAAGGGCCTCGTG

ATACGCCTATTTTTATAGGTTAATGTCATGATAATAATGGTTTCTTAGACGTCAGGTG

GCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAA

AAGGAAGAGTATGAGTATTCAACATTTCCGTGTCGCCCTTATTCCCTTTTTTGCGGCA

TTTTGCCTTCCTGTTTTTGCTCACCCAGAAACGCTGGTGAAAGTAAAAGATGCTGAA

GATCAGTTGGGTGCACGAGTGGGTTACATCGAACTGGATCTCAACAGCGGTAAGAT

CCTTGAGAGTTTTCGCCCCGAAGAACGTTTTCCAATGATGAGCACTTTTAAAGTTCT

GCTATGTGGCGCGGTATTATCCCGTATTGACGCCGGGCAAGAGCAACTCGGTCGCCG

CATACACTATTCTCAGAATGACTTGGTTGAGTACTCACCAGTCACAGAAAAGCATCT

TACGGATGGCATGACAGTAAGAGAATTATGCAGTGCTGCCATAACCATGAGTGATA

ACACTGCGGCCAACTTACTTCTGACAACGATCGGAGGACCGAAGGAGCTAACCGCT

TTTTTGCACAACATGGGGGATCATGTAACTCGCCTTGATCGTTGGGAACCGGAGCTG

AATGAAGCCATACCAAACGACGAGCGTGACACCACGATGCCTGTAGCAATGGCAAC

AACGTTGCGCAAACTATTAACTGGCGAACTACTTACTCTAGCTTCCCGGCAACAATT

AATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGAC

GGGGAGTCAGGCAACTATGGATGAACGAAATAGACAGATCGCTGAGATAGGTGCCT

CACTGATTAAGCATTGGTAACTGTCAGACCAAGTTTACTCATATATACTTTAGATTG

ATTTAAAACTTCATTTTTAATTTAAAAGGATCTAGGTGAAGATCCTTTTTGATAATCT

CATGACCAAAATCCCTTAACGTGAGTTTTCGTTCCACTGAGCGTCAGACCCCGTAGA

AAAGATCAAAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCTACCAAC

TCTTTTTCCGAAGGTAACTGGCTTCAGCAGAGCGCAGATACCAAATACTGTCCTTCT

AGTGTAGCCGTAGTTAGGCCACCACTTCAAGAACTCTGTAGCACCGCCTACATACCT

CGCTCTGCTAATCCTGTTACCAGTGGCTGCTGCCAGTGGCGATAAGTCGTGTCTTAC

CGGGTTGGACTCAAGACGATAGTTACCGGATAAGGCGCAGCGGTCGGGCTGAACGG

GGGGTTCGTGCACACAGCCCAGCTTGGAGCGAACGACCTACACCGAACTGAGATAC

CTACAGCGTGAGCTATGAGAAAGCGCCACGCTTCCCGAAGGGAGAAAGGCGGACA

GGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCG

TCGATTTTTGTGATGCTCGTCAGGGGGCGGAGCCTATGGAAAAACGCCAGCAACG

CGGCCTTTTTACGGTTCCTGGCCTTTTGCTGGCCTTTTGCTCACATGTTCTTTCCTGCG

TTATCCCCTGATTCTGTGGATAACCGTATTACCGCCTTTGAGTGAGCTGATACCGCTC

GCCGCAGCCGAACGACCGAGCGCAGCGAGTCAGTGAGCGAGGAAGCGGAAGAGCG

CCCAATACGCAAACCGCCTCTCCCCGCGCGTTGGCCGATTCATTAATGCAGCTGCGC
```

-continued

```
GCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCA

CTAGGGGTTCCTTGTAGTTAATGATTAACCCGCCATGCTACTTATCTACGTAGCCATG

CTCTAGGACATTGATTATTGACTAGTGGAGTTCCGCGTTACATAACTTACGGTAAAT

GGCCCGCCTGGCTGACCGCCCAACGACCCCCGCCCATTGACGTCAATAATGACGTAT

GTTCCCATAGTAACGCCAATAGGGACTTTCCATTGACGTCAATGGGTGGAGTATTTA

CGGTAAACTGCCCACTTGGCAGTACATCAAGTGTATCATATGCCAAGTACGCCCCCT

ATTGACGTCAATGACGGTAAATGGCCCGCCTGGCATTATGCCCAGTACATGACCTTA

TGGGACTTTCCTACTTGGCAGTACATCTACGTATTAGTCATCGCTATTACCATGGTCG

AGGTGAGCCCCACGTTCTGCTTCACTCTCCCCATCTCCCCCCCCTCCCCACCCCCAAT

TTTGTATTTATTTATTTTTTAATTATTTTGTGCAGCGATGGGGGCGGGGGGGGGGGG

GGGCGCGCGCCAGGCGGGGCGGGGGGGCGAGGGGCGGGGCGGGGCGAGGCGG

AGAGGTGCGGCGGCAGCCAATCAGAGCGGCGCGCTCCGAAAGTTTCCTTTTATGGC

GAGGCGGCGGCGGCGGCGGCCCTATAAAAAGCGAAGCGCGCGGCGGGCGGGAGTC

GCTGCGCGCTGCCTTCGCCCCGTGCCCCGCTCCGCCGCCGCCTCGCGCCGCCCGCCC

CGGCTCTGACTGACCGCGTTACTAAAACAGGTAAGTCCGGCCTCCGCGCCGGGTTTT

GGCGCCTCCCGCGGGCGCCCCCCTCCTCACGGCGAGCGCTGCCACGTCAGACGAAG

GGCGCAGCGAGCGTCCTGATCCTTCCGCCCGGACGCTCAGGACAGCGGCCCGCTGC

TCATAAGACTCGGCCTTAGAACCCCAGTATCAGCAGAAGGACATTTTAGGACGGGA

CTTGGGTGACTCTAGGGCACTGGTTTTCTTTCCAGAGAGCGGAACAGGCGAGGAAA

AGTAGTCCCTTCTCGGCGATTCTGCGGAGGGATCTCCGTGGGGCGGTGAACGCCGAT

GATGCCTCTACTAACCATGTTCATGTTTTCTTTTTTTTTCTACAGGTCCTGGGTGACG

AACAGGGTACC 3'
```

SEQ ID NO. 2 (mRNA expression cassette No. 2 - p53).

```
5' GCCACCATGGAAGAACCGCAGAGCGATCCGAGCGTGGAACCGCCGCTGAGCCAGG

AAACCTTTAGCGATCTGTGGAAACTGCTGCCGGAAAACAACGTGCTGAGCCCGCTG

CCGAGCCAGGCGATGGATGATCTGATGCTGAGCCCGGATGATATTGAACAGTGGTTT

ACCGAAGATCCGGGCCCGGATGAAGCGCCGCGCATGCCGGAAGCGGCGCCGCCGGT

GGCGCCGGCGCCGGCGGCGCCGACCCCGGCGGCGCCGGCGCCGGCGCCGAGCTGGC

CGCTGAGCAGCAGCGTGCCGAGCCAGAAAACCTATCAGGGCAGCTATGGCTTTCGC

CTGGGCTTTCTGCATAGCGGCACCGCGAAAAGCGTGACCTGCACCTATAGCCCGGC

GCTGAACAAAATGTTTTGCCAGCTGGCGAAAACCTGCCCGGTGCAGCTGTGGGTGG

ATAGCACCCCGCCGCCGGGCACCCGCGTGCGCGCGATGGCGATTTATAAACAGAGC

CAGCATATGACCGAAGTGGTGCGCCGCTGCCCGCATCATGAACGCTGCAGCGATAG

CGATGGCCTGGCGCCGCCGCAGCATCTGATTCGCGTGGAAGGCAACCTGCGCGTGG

AATATCTGGATGATCGCAACACCTTTCGCCATAGCGTGGTGGTGCCGTATGAACCGC

CGGAAGTGGGCAGCGATTGCACCACCATTCATTATAACTATATGTGCAACAGCAGCT

GCATGGGCGGCATGAACCGCCGCCCGATTCTGACCATTATTACCCTGGAAGATAGC

AGCGGCAACCTGCTGGGCCGCAACAGCTTTGAAGTGCGCGTGTGCGCGTGCCCGGG

CCGCGATCGCCGCACCGAAGAAGAAACCTGCGCAAAAAAGGCGAACCGCATCAT

GAACTGCCGCCGGGCAGCACCAAACGCGCGCTGCCGAACAACACCAGCAGCAGCCC
```

```
                                 -continued
GCAGCCGAAAAAAAAACCGCTGGATGGCGAATATTTTACCCTGCAGATTCGCGGCC

GCGAACGCTTTGAAATGTTTCGCGAACTGAACGAAGCGCTGGAACTGAAAGATGCG

CAGGCGGGCAAAGAACCGGGCGGCAGCCGCGCGCATAGCAGCCATCTGAAAAGCA

AAAAAGGCCAGAGCACCAGCCGCCATAAAAAACTGATGTTTAAAACCGAAGGCCCG

GATAGCGATT 3'

SEQ ID NO. 3 = SEQ ID NO. 1 + SEQ ID NO. 2
5' GCCACCATGGAAGAACCGCAGAGCGATCCGAGCGTGGAACCGCCGCTGAGCCAGG

AAACCTTTAGCGATCTGTGGAAACTGCTGCCGGAAAACAACGTGCTGAGCCCGCTG

CCGAGCCAGGCGATGGATGATCTGATGCTGAGCCCGGATGATATTGAACAGTGGTTT

ACCGAAGATCCGGGCCCGGATGAAGCGCCGCGCATGCCGGAAGCGGCGCCGCCGGT

GGCGCCGGCGCCGGCGGCGCCGACCCCGGCGGCGCCGGCGCCGGCGCCGAGCTGGC

CGCTGAGCAGCAGCGTGCCGAGCCAGAAAACCTATCAGGGCAGCTATGGCTTTCGC

CTGGGCTTTCTGCATAGCGGCACCGCGAAAAGCGTGACCTGCACCTATAGCCCGGC

GCTGAACAAAATGTTTTGCCAGCTGGCGAAAACCTGCCCGGTGCAGCTGTGGGTGG

ATAGCACCCCGCCGCCGGGCACCCGCGTGCGCGCGATGGCGATTTATAAACAGAGC

CAGCATATGACCGAAGTGGTGCGCCGCTGCCCGCATCATGAACGCTGCAGCGATAG

CGATGGCCTGGCGCCGCCGCAGCATCTGATTCGCGTGGAAGGCAACCTGCGCGTGG

AATATCTGGATGATCGCAACACCTTTCGCCATAGCGTGGTGGTGCCGTATGAACCGC

CGGAAGTGGGCAGCGATTGCACCACCATTCATTATAACTATATGTGCAACAGCAGCT

GCATGGGCGGCATGAACCGCCGCCCGATTCTGACCATTATTACCCTGGAAGATAGC

AGCGGCAACCTGCTGGGCCGCAACAGCTTTGAAGTGCGCGTGTGCGCGTGCCCGGG

CCGCGATCGCCGCACCGAAGAAGAAAACCTGCGCAAAAAAGGCGAACCGCATCAT

GAACTGCCGCCGGGCAGCACCAAACGCGCGCTGCCGAACAACACCAGCAGCAGCCC

GCAGCCGAAAAAAAAACCGCTGGATGGCGAATATTTTACCCTGCAGATTCGCGGCC

GCGAACGCTTTGAAATGTTTCGCGAACTGAACGAAGCGCTGGAACTGAAAGATGCG

CAGGCGGGCAAAGAACCGGGCGGCAGCCGCGCGCATAGCAGCCATCTGAAAAGCA

AAAAAGGCCAGAGCACCAGCCGCCATAAAAAACTGATGTTTAAAACCGAAGGCCCG

GATAGCGATTTCTAGAAAGATCTAACTTGTTTATTGCAGCTTATAATGGTTACAAAT

AAAGCAATAGCATCACAAATTTCACAAATAAAGCATTTTTTTCACTGCATTCTAGTT

GTGGTTTGTCCAAACTCATCAATGTATCTTATCATGTCTGGATCTCGACCTCGACTAG

AGCATGGCTACGTAGATAAGTAGCATGGCGGGTTAATCATTAACTACAAGGAACCC

CTAGTGATGGAGTTGGCCACTCCCTCTCTGCGCGCTCGCTCGCTCACTGAGGCCGGG

CGACCAAAGGTCGCCCGACGCCCGGGCTTTGCCCGGGCGGCCTCAGTGAGCGAGCG

AGCGCGCAGCTGGCGTAATAGCGAAGAGGCCCGCACCGATCGCCCTTCCCAACAGT

TGCGCAGCCTGAATGGCGAATGGCGATTCCGTTGCAATGGCTGGCGGTAATATTGTT

CTGGATATTACCAGCAAGGCCGATAGTTTGAGTTCTTCTACTCAGGCAAGTGATGTT

ATTACTAATCAAAGAAGTATTGCGACAACGGTTAATTTGCGTGATGGACAGACTCTT

TTACTCGGTGGCCTCACTGATTATAAAAACACTTCTCAGGATTCTGGCGTACCGTTCC

TGTCTAAAATCCCTTTAATCGGCCTCCTGTTTAGCTCCCGCTCTGATTCTAACGAGGA

AAGCACGTTATACGTGCTCGTCAAAGCAACCATAGTACGCGCCCTGTAGCGGCGCA

TTAAGCGCGGCGGGTGTGGTGGTTACGCGCAGCGTGACCGCTACACTTGCCAGCGC
```

-continued

```
CCTAGCGCCCGCTCCTTTCGCTTTCTTCCCTTCCTTTCTCGCCACGTTCGCCGGCTTTC
CCCGTCAAGCTCTAAATCGGGGGCTCCCTTTAGGGTTCCGATTTAGTGCTTTACGGC
ACCTCGACCCCAAAAAACTTGATTAGGGTGATGGTTCACGTAGTGGGCCATCGCCCT
GATAGACGGTTTTTCGCCCTTTGACGTTGGAGTCCACGTTCTTTAATAGTGGACTCTT
GTTCCAAACTGGAACAACACTCAACCCTATCTCGGTCTATTCTTTTGATTTATAAGGG
ATTTTGCCGATTTCGGCCTATTGGTTAAAAAATGAGCTGATTTAACAAAAATTTAAC
GCGAATTTTAACAAAATATTAACGTTTACAATTTAAATATTTGCTTATACAATCTTCC
TGTTTTTGGGGCTTTTCTGATTATCAACCGGGGTACATATGATTGACATGCTAGTTTT
ACGATTACCGTTCATCGATTCTCTTGTTTGCTCCAGACTCTCAGGCAATGACCTGATA
GCCTTTGTAGAGACCTCTCAAAAATAGCTACCCTCTCCGGCATGAATTTATCAGCTA
GAACGGTTGAATATCATATTGATGGTGATTTGACTGTCTCCGGCCTTTCTCACCCGTT
TGAATCTTTACCTACACATTACTCAGGCATTGCATTTAAAATATATGAGGGTTCTAA
AAATTTTTATCCTTGCGTTGAAATAAAGGCTTCTCCCGCAAAAGTATTACAGGGTCA
TAATGTTTTTGGTACAACCGATTTAGCTTTATGCTCTGAGGCTTTATTGCTTAATTTT
GCTAATTCTTTGCCTTGCCTGTATGATTTATTGGATGTTGGAATTCCTGATGCGGTAT
TTTCTCCTTACGCATCTGTGCGGTATTTCACACCGCATATGGTGCACTCTCAGTACAA
TCTGCTCTGATGCCGCATAGTTAAGCCAGCCCCGACACCCGCCAACACCCGCTGACG
CGCCCTGACGGGCTTGTCTGCTCCCGGCATCCGCTTACAGACAAGCTGTGACCGTCT
CCGGGAGCTGCATGTGTCAGAGGTTTTCACCGTCATCACCGAAACGCGCGAGACGA
AAGGGCCTCGTGATACGCCTATTTTTATAGGTTAATGTCATGATAATAATGGTTTCTT
AGACGTCAGGTGGCACTTTTCGGGGAAATGTGCGCGGAACCCCTATTTGTTTATTTT
TCTAAATACATTCAAATATGTATCCGCTCATGAGACAATAACCCTGATAAATGCTTC
AATAATATTGAAAAAGGAAGAGTATGAGTATTCAACATTTCCGTGTCGCCCTTATTC
CCTTTTTTGCGGCATTTTGCCTTCCTGTTTTTGCTCACCCAGAAACGCTGGTGAAAGT
AAAAGATGCTGAAGATCAGTTGGGTGCACGAGTGGGTTACATCGAACTGGATCTCA
ACAGCGGTAAGATCCTTGAGAGTTTTCGCCCCGAAGAACGTTTTCCAATGATGAGCA
CTTTTAAAGTTCTGCTATGTGGCGCGGTATTATCCCGTATTGACGCCGGGCAAGAGC
AACTCGGTCGCCGCATACACTATTCTCAGAATGACTTGGTTGAGTACTCACCAGTCA
CAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAA
GGAGCTAACCGCTTTTTTGCACAACATGGGGGATCATGTAACTCGCCTTGATCGTTG
GGAACCGGAGCTGAATGAAGCCATACCAAACGACGAGCGTGACACCACGATGCCTG
TAGCAATGGCAACAACGTTGCGCAAACTATTAACTGGCGAACTACTTACTCTAGCTT
CCCGGCAACAATTAATAGACTGGATGGAGGCGGATAAAGTTGCAGGACCACTTCTG
CGCTCGGCCCTTCCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATCGTA
GTTATCTACACGACGGGGAGTCAGGCAACTATGGATGAACGAAATAGACAGATCGC
TGAGATAGGTGCCTCACTGATTAAGCATTGGTAACTGTCAGACCAAGTTTACTCATA
TATACTTTAGATTGATTTAAAACTTCATTTTTAATTTAAAAGGATCTAGGTGAAGATC
CTTTTTGATAATCTCATGACCAAAATCCCTTAACGTGAGTTTTCGTTCCACTGAGCGT
CAGACCCCGTAGAAAAGATCAAAGGATCTTCTTGAGATCCTTTTTTTCTGCGCGTAA
```

-continued

```
TCTGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATACCAA
ATACTGTCCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGG
TCGGGCTGAACGGGGGGTTCGTGCACACAGCCCAGCTTGGAGCGAACGACCTACAC
CGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAG
GGAGCTTCCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTATGGAAAAA
CGCCAGCAACGCGGCCTTTTTACGGTTCCTGGCCTTTTGCTGGCCTTTTGCTCACATG
TTCTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGGAA
GCGGAAGAGCGCCCAATACGCAAACCGCCTCTCCCCGCGCGTTGGCCGATTCATTA
ATGCAGCTGCGCGCTCGCTCGCTCACTGAGGCCGCCCGGGCAAAGCCCGGGCGTCG
GGCGACCTTTGGTCGCCCGGCCTCAGTGAGCGAGCGAGCGCGCAGAGAGGGAGTGG
CCAACTCCATCACTAGGGGTTCCTTGTAGTTAATGATTAACCCGCCATGCTACTTATC
TACGTAGCCATGCTCTAGGACATTGATTATTGACTAGTGGAGTTCCGCGTTACATAA
CTTACGGTAAATGGCCCGCCTGGCTGACCGCCCAACGACCCCCGCCCATTGACGTCA
ATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCA
AGTACGCCCCCTATTGACGTCAATGACGGTAAATGGCCCGCCTGGCATTATGCCCAG
TACATGACCTTATGGGACTTTCCTACTTGGCAGTACATCTACGTATTAGTCATCGCTA
TTACCATGGTCGAGGTGAGCCCCACGTTCTGCTTCACTCTCCCCATCTCCCCCCCCTC
CCCACCCCCAATTTTGTATTTATTTATTTTTTAATTATTTTGTGCAGCGATGGGGGCG
GGGGGGGGGGGGGCGCGCGCCAGGCGGGGGGGGCGGGGCGAGGGGCGGGGCG
GGGCGAGGCGGAGAGGTGCGGCGGCAGCCAATCAGAGCGGCGCGCTCCGAAAGTT
TCCTTTTATGGCGAGGCGGCGGCGGCGGCGGCCCTATAAAAAGCGAAGCGCGCGGC
GGGCGGGAGTCGCTGCGCGCTGCCTTCGCCCCGTGCCCCGCTCCGCCGCCGCCTCGC
GCCGCCCGCCCCGGCTCTGACTGACCGCGTTACTAAAACAGGTAAGTCCGGCCTCCG
CGCCGGGTTTTGGCGCCTCCCGCGGGCGCCCCCCTCCTCACGGCGAGCGCTGCCACG
TCAGACGAAGGGCGCAGCGAGCGTCCTGATCCTTCCGCCCGGACGCTCAGGACAGC
GGCCCGCTGCTCATAAGACTCGGCCTTAGAACCCCAGTATCAGCAGAAGGACATTTT
AGGACGGGACTTGGGTGACTCTAGGGCACTGGTTTTCTTTCCAGAGAGCGGAACAG
GCGAGGAAAAGTAGTCCCTTCTCGGCGATTCTGCGGAGGGATCTCCGTGGGGCGGT
GAACGCCGATGATGCCTCTACTAACCATGTTCATGTTTCTTTTTTTTCTACAGGTC
CTGGGTGACGAACAGGGTACC 3'
```

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3 or at the 5' end of SEQ ID NO. 1.

As will be appreciated by those skilled in the art, a perfect match of nucleotides with each of the expression cassette sequences is not necessary in order to have the desired result of increased bioavailability of the target biomolecule as a result of the target cell mRNA of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1—Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified and the bands on interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes are integrated with the pAVA-00200 backbone via homologous recombination. The resulting RP contained the following: 5' ITR, CASI promoter, mRNA expression cassette, WPRE, SV40 polyA and ITR 3'.

The invention claimed is:

1. A composition that comprises a recombinant plasmid (RP) with a sequence of nucleotides that comprise a start region, an end region and an insert sequence positioned between the start region and the end region, in which the insert sequence encodes for a sequence of messenger ribonucleic acid (mRNA) that encodes for a protein, wherein the insert sequence is SEQ ID NO. 2.

2. The composition of claim 1, wherein the sequence of nucleotides is configured to be delivered to a target cell that has an under-expressed or mis-expressed biomolecule, wherein the sequence of nucleotides is encased in a protein coat, a lipid vesicle, or any combination thereof.

3. The composition of claim 1, wherein the sequence of nucleotides is configured to be delivered to a target cell that has an under-expressed or mis-expressed biomolecule, wherein the sequence of nucleotides is encased in a viral vector.

4. The compositions of claim 3, wherein the viral vector is a double stranded DNA virus, a single stranded DNA virus, a single stranded RNA virus, or a double stranded RNA virus.

5. The compositions of claim 3, wherein the viral vector is an adeno-associated virus.

6. The composition of claim 1, wherein the protein is p53.

7. A composition that comprises a recombinant protein (RP) with a sequence of nucleotides for encoding a sequence of messenger ribonucleic acid (mRNA) that that encodes for a protein, wherein the sequence is SEQ ID NO. 3.

* * * * *

SEQUENCE LISTING

```
Sequence total quantity: 3
SEQ ID NO: 1           moltype = DNA   length = 5193
FEATURE                Location/Qualifiers
source                 1..5193
                       mol_type = other DNA
                       organism = synthetic construct
SEQUENCE: 1
tctagaaaga tctaacttgt ttattgcagc ttataatggt tacaaataaa gcaatagcat   60
cacaaatttc acaaataaag catttttttc actgcattct agttgtggtt tgtccaaact  120
catcaatgta tcttatcatg tctggatctc gacctcgact agagcatggc tacgtagata  180
agtagcatgg cgggttaatc attaactaca aggaacccct agtgatggag ttggccactc  240
cctctctgcg cgctcgctcg ctcactgagg ccgggcgacc aaaggtcgcc cgacgcccgg  300
gctttgcccg ggcggcctca gtgagcgagc gagcgcgcag ctggcgtaat agcgaagagg  360
cccgcaccga tcgcccttcc caacagttgc gcagcctgaa tggcgaatgg cgattccgtt  420
gcaatggctg cgcgtaatat tgttctggat attaccagca aggccgatag tttgagttct  480
tctactcagg caagtgatgt tattactaat caaagaagta ttgcgacaac ggttaatttg  540
cgtgatggac agactctttt actcggtggc ctcactgatt ataaaaacac ttctcaggat  600
tctggcgtac cgttcctgtc taaatcccct ttaatcggcc tcctgtttag ctcccgctct  660
gattctaacg aggaaagcac gttatacgtg ctcgtcaaag caaccatagt acgcgccctg  720
tagcggcgca ttaagcgcgg cgggtgtggt ggttacgcgc agcgtgaccg ctacacttgc  780
cagcgcccta gcgcccgctc ctttcgcttt cttcccttcc tttctcgcca cgttcgccgg  840
ctttccccgt caagctctaa atcggggggct ccctttaggg ttccgattta gtgctttacg  900
gcacctcgac cccaaaaaac ttgattaggg tgatggttca cgtagtgggc catcgccctg  960
atagacggtt tttcgccctt tgacgttgga gtccacgttc tttaatagtg actcttgtt  1020
ccaaactgga acaacactca accctatctc ggtctattct tttgatttat aagggatttt  1080
gccgatttcg gcctattggt taaaaaatga gctgatttaa caaaaattta acgcgaattt  1140
taacaaaata ttaacgttta caatttaaat atttgcttat acaatcttcc tgttttgg   1200
gctttctga ttatcaaccg gggtacatat gattgacatg ctagttttac gattaccgtt  1260
catcgattct cttgtttgct ccagactctc aggcaatgac ctgatagcct ttgtagagac  1320
ctctcaaaaa tagctaccct ctccggcatg aatttatcag ctagaacggt tgaatatcat  1380
attgatggtg atttgactgt ctccggcctt tctcacccgt ttgaatcttt acctacacat  1440
tactcaggca ttgcatttaa aatatatgag ggttctaaaa attttatcc ttgcgttgaa  1500
ataaaggctt ctcccgcaaa agtattacag ggtcataatg ttttggtac aaccgattta  1560
gctttatgct ctgaggcttt attgcttaat tttgctattt ctttgccttg cctgtatgat  1620
ttattggatg ttggaattcc tgatgcggta ttttctcctt acgcatctgt gcggtatttc  1680
acaccgcata tggtgcactc tcagtacaat ctgctctgat gccgcatagt taagccagcc  1740
ccgacacccg ccaacacccg ctgacgcgcc ctgacgggct tgtctgctcc cggcatccgc  1800
ttacagacaa gctgtgaccg tctccggag ctgcatgcgt cagaggtttt caccgtcatc  1860
accgaaacgc gcgagacgaa agggcctcgt gatacgccta ttttttatagg ttaatgtcat  1920
gataataatg gtttcttaga cgtcaggtgg cacttttcgg ggaaatgtgc gcggaacccc  1980
tatttgttta tttttctaaa tacattcaaa tatgtatccg ctcatgagac aataaccctg  2040
ataaatgctt caataatatt gaaaaaggaa gagtatgagt attcaacatt tccgtgtcgc  2100
ccttattccc ttttttgcgg catttgcct tcctgtttt gctcacccag aaacgctggt  2160
gaaagtaaaa gatgctgaag atcagttggg tgcacgagtg ggttacatcg aactggatct  2220
caacagcggt aagatccttg agagttttcg ccccgaagaa cgttttccaa tgatgagcac  2280
ttttaaagtt ctgctatgtg gcgcggtatt atcccgtatt gacgccgggc aagagcaact  2340
cggtcgccgc atacactatt ctcagaatga cttggttgag tactcaccag tcacagaaaa  2400
gcatcttacg gatggcatga cagtaagaga attatgcagt gctgccataa ccatgagtga  2460
taacactgcg gccaacttac ttctgacaac gatcggagga ccgaaggagc taaccgcttt  2520
tttgcacaac atggggggatc atgtaactcg ccttgatcgt tgggaaccgg agctgaatga  2580
agccatacca aacgacgagc gtgacaccac gatgcctgta gcaatggcaa caacgttgcg  2640
caaactatta actggcgaac tacttactct agcttcccgg caacaattaa tagactggat  2700
ggaggcggat aaagttgcag gaccacttct gcgctcggcc cttccggctg gctggtttat  2760
```

```
tgctgataaa tctggagccg gtgagcgtgg gtctcgcggt atcattgcag cactggggcc    2820
agatggtaag ccctcccgta tcgtagttat ctacacgacg gggagtcagg caactatgga    2880
tgaacgaaat agacagatcg ctgagatagg tgcctcactg attaagcatt ggtaactgtc    2940
agaccaagtt tactcatata tactttagat tgatttaaaa cttcattttt aatttaaaag    3000
gatctaggtg aagatccttt ttgataatct catgaccaaa atcccttaac gtgagttttc    3060
gttccactga gcgtcagacc ccgtagaaaa gatcaaagga tcttcttgag atcctttttt    3120
tctgcgcgta atctgctgct tgcaaacaaa aaaaccaccg ctaccagcgg tggtttgttt    3180
gccggatcaa gagctaccaa ctcttttttcc gaaggtaact ggcttcagca gagcgcagat    3240
accaaatact gtccttctag tgtagccgta gttaggccac cacttcaaga actctgtagc    3300
accgcctaca tacctcgctc tgctaatcct gttaccagtg gctgctgcca gtggcgataa    3360
gtcgtgtctt accgggttgg actcaagacg atagttaccg gataaggcgc agcggtcggg    3420
ctgaacgggg ggttcgtgca cacagcccag cttggagcga acgacctaca ccgaactgag    3480
atacctacag cgtgagctat gagaaagcgc cacgcttccc gaagggagaa aggcggacag    3540
gtatccggta agcggcaggg tcggaacagg agagcgcacg aggggagctt ccagggggaaa    3600
cgcctggtat ctttatagtc ctgtcgggtt tcgccacctc tgacttgagc gtcgattttt    3660
gtgatgctcg tcaggggggc ggagcctatg gaaaaacgcc agcaacgcgg cctttttacg    3720
gttcctggcc ttttgctggc cttttgctca catgttcttt cctgcgttat cccctgattc    3780
tgtggataac cgtattaccg ccttttgagtg agctgatacc gctcgccgca gccgaacgac    3840
cgagcgcagc gagtcagtga gcgaggaagc ggaagagcgc ccaatacgca aaccgcctct    3900
ccccgcgcgt tggccgattc attaatgcag ctgcgcgctc gctcgctcac tgaggccgcc    3960
cgggcaaagc ccgggcgtcg ggcgaccttt ggtcgcccgg cctcagtgag cgagcgagcg    4020
cgcagagagg gagtggccaa ctccatcact aggggttcct tgtagttaat gattaaccga    4080
ccatgctact tatctacgta gccatgctct aggacattga ttattgacta gtggagttcc    4140
gcgttacata acttacggta aatggcccgc ctggctgacc gcccaacgac ccccgcccat    4200
tgacgtcaat aatgacgtat gttcccatag taacgccaat agggactttc cattgacgtc    4260
aatgggtgga gtatttacgg taaactgccc acttggcagt acatcaagtg tatcatatgc    4320
caagtacgcc ccctattgac gtcaatgacg gtaaatggcc cgcctggcat tatgcccagt    4380
acatgacctt atgggacttt cctacttggc agtacatcta cgtattagtc atcgctatta    4440
ccatggtcga ggtgagcccc acgttctgct tcactctccc catctccccc cctccccac     4500
ccccaattttt gtatttattt ttttttaat tattttgtgc agcgatgggg gcggggggggg     4560
gggggggcgc gcgccaggcg gggcggggc gggcgagggg cggggcgggg cgaggcggaa     4620
aggtgcggcg gcagccaatc agagcggcgc gctccgaaag tttccttttta tggcgaggcg     4680
gcggcggcg cggccctata aaagcgaag cgcgcggcgg gcgggagtcg ctgcgcgctg     4740
ccttcgcccc gtgccccgct ccgccgccgc ctcgcgccgc ccgccccggc tctgactgac     4800
cgcgttacta aaacaggtaa gtccggcctc gcgccgggt tttgcgcct cccgcgggcc     4860
ccccctcct cacggcgagc gctgccacgt cagacgaagg gcgcagcgcg cgtcctgatc     4920
cttccgcccg gacgctcagg acagcggccc gctgctcata agactcggcc ttagaaccc     4980
agtatcagca gaaggacatt ttaggacggg acttgggtga ctctagggca ctggttttct     5040
ttccagagag cggaacaggc gaggaaaagt agtcccttct cggcgattct gcggagggat     5100
ctccgtgggg cggtgaacgc cgatgatgcc tctactaacc atgttcatgt tttctttttt    5160
tttctacagg tcctgggtga cgaacagggt acc                                  5193

SEQ ID NO: 2         moltype = DNA  length = 1186
FEATURE              Location/Qualifiers
source               1..1186
                     mol_type = other DNA
                     organism = synthetic construct
SEQUENCE: 2
gccaccatgg aagaaccgca gagcgatccg agcgtggaac cgccgctgag ccaggaaacc     60
tttagcgatc tgtggaaact gctgccggaa acaacgtgc tgagcccgct gccgagccag    120
gcgatggatg atctgatgct gagcccggat gatattgaac agtggtttac cgaagatccg    180
ggcccggatg aagcgccgcg catgccggaa gcggcgccgc cggtggcgcc ggcgccggcg    240
gcgccgaccc cggcggcgcc ggcgccggcg ccgagctggc cgctgagcag cagcgtgccg    300
agccagaaaa cctatcaggg cagctatggc tttcgcctgg gctttctgca tagcggcacc    360
gcgaaaagcg tgacctgcac ctatagcccg gcgctgaaca aaatgttttg ccagctggcg    420
aaaacctgcc cggtgcagct gtgggtggat agcaccccgc cgccgggcac ccgcgtgcgc    480
gcgatggcga tttataaaca gagccagcat atgaccgaag tggtgcgccg ctgcccgcat    540
catgaacgct gcagcgatag cgatggcctg gcgccgccgc agcatctgat tcgcgtggaa    600
ggcaacctgc gcgtggaata tctggatgat cgcaacacct ttcgccatag cgtggtggtg    660
ccgtatgaac cgccggaagt ggcagcgat tgcaccacca ttcattataa ctatatgtgc    720
aacagcagct gcatgggcgg catgaaccgc cgcccgattc tgaccattat taccctggaa    780
gatagcagcg gcaacctgct gggccgcaac agctttgaag tgcgcgtgtg cgcgtgcccg    840
ggccgcgatc gccgcaccga agaagaaaac ctgcgcaaaa aaggcgaacc gcatcatgaa    900
ctgccgccgg gcagcaccaa acgcgcgctg ccgaacaaca cagcagcag cccgcagccg    960
aaaaaaaaac cgctgatgg cgaatatttt accctgcaga ttcgcggccg aacgctttt    1020
gaaatgtttc gcgaactgaa cgaagcgctg gaactgaaaa tgcgcaggc gggcaaagaa    1080
ccgggcggca gccgcgcgca tagcagccat ctgaaaagca aaaaggcca gagcaccagc    1140
cgccataaaa aactgatgtt taaaaccgaa ggcccgata gcgatt                    1186

SEQ ID NO: 3         moltype = DNA  length = 6379
FEATURE              Location/Qualifiers
source               1..6379
                     mol_type = other DNA
                     organism = synthetic construct
SEQUENCE: 3
gccaccatgg aagaaccgca gagcgatccg agcgtggaac cgccgctgag ccaggaaacc     60
tttagcgatc tgtggaaact gctgccggaa acaacgtgc tgagcccgct gccgagccag    120
gcgatggatg atctgatgct gagcccggat gatattgaac agtggtttac cgaagatccg    180
ggcccggatg aagcgccgcg catgccggaa gcggcgccgc cggtggcgcc ggcgccggcg    240
```

```
gcgccgaccc cggcggcgcc ggcgccggcg ccgagctggc cgctgagcag cagcgtgccg  300
agccagaaaa cctatcaggg cagctatggc tttcgcctgg gctttctgca tagcggcacc  360
gcgaaaagcg tgacctgcac ctatagcccg cgctgaaca aaatgttttg ccagctggcg  420
aaaacctgcc cggtgcagct gtgggtggat agcaccccgc cgccgggcac ccgcgtgcgc  480
gcgatggcga tttataaaca gagccagcat atgaccgaag tggtgcgccg ctgcccgcat  540
catgaacgct gcagcgatag cgatggcctg cgccgccgc agcatctgat tcgcgtggaa  600
ggcaacctgc gcgtggaata tctgatgat cgcaacacct ttcgccatag cgtggtggtg  660
ccgtatgaac cgccggaagt gggcagcgat tgcaccacca ttcattataa ctatatgtgc  720
aacagcagct gcatgggcgg catgaaccgc cgcccgattc tgaccattat taccctggaa  780
gatagcagcg gcaacctgct gggccgcaac agctttgaag tgcgcgtgtg cgcgtgcccg  840
ggccgcgatc gccgcaccga agaagaaaac ctgcgcaaaa aaggcgaacc gcatcatgaa  900
ctgccgccgg gcagcaccaa acgcgcgctg ccgaacaaca ccagcagcag cccgcagccg  960
aaaaaaaaac cgctggatgg cgaatatttt accctgcaga ttcgcggccg cgaacgcttt  1020
gaaatgtttc gcgaactgaa cgaagcgctg gaactgaaga atgcgcaggc gggcaaagaa  1080
ccgggcggca gccgcgcgca tagcagccat ctgaaaagca aaaaaggcca gagcaccagc  1140
cgccataaaa aactgatgtt taaaaccgaa ggccccggata gcgatttcta aaagatcta  1200
acttgttttat tgcagcttat aatggttaca aataaagcaa tagcatcaca aatttcacaa  1260
ataaagcatt ttttttcactg cattctagtt gtggttttgtc caaactcatc aatgtatctt  1320
atcatgtctg gatctcgacc tcgactagag catggctacg tagataagta gcatggcggg  1380
ttaatcatta actacaagga acccctagtg atggagttgg ccactccctc tctgcgcgct  1440
cgctcgctca ctgaggccgg gcgaccaaag gtcgcccgac gcccgggctt tgcccggggc  1500
gcctcagtga gcgagcagc gcgcagctgg cgtaatagcg aagaggcccg caccgatcgc  1560
ccttcccaac agttgcgcag cctgaatggc gaatggcgat tccgttgcaa tggctggcgg  1620
taatattgtt ctggatatta ccagcaaggc cgatagtttg agtcttcta ctcaggcaag  1680
tgatgttatt actaatcaaa gaagtattgc gacaacggtt aatttgcgtg atggacagac  1740
tcttttactc ggtggcctca ctgattataa aaacacttct caggattctg gcgtaccgtt  1800
cctgtctaaa atccctttaa tcggcctcct gtttagctcc cgctctgatt ctaacgagga  1860
aagcacgtta tacgtgctcg tcaaagcaac catagtacgc gccctgtagc ggcgcattaa  1920
gcgcggcggg tgtggtggtt acgcgcagcg tgaccgctac acttgccagc gccctagcgc  1980
ccgctccttt cgctttcttc ccttcctttc tcgccacgtt cgccggcttt ccccgtcaag  2040
ctctaaatcg ggggctccct ttagggttcc gatttagtgc tttacggcac ctcgacccca  2100
aaaaacttga ttagggtgat ggttcacgta gtgggccatc gccctgatag acggtttttc  2160
gccctttgac gttggagtcc acgttcttta atagtggact cttgttccaa actggaacaa  2220
cactcaaccc tatctcggtc tattcttttg atttataagg gattttgccg atttcggcct  2280
attggttaaa aaatgagctg atttaacaaa aatttaacgc gaatttaac aaaatattaa  2340
cgtttacaat ttaaatattt gcttatacaa tcttcctgtt tttggggctt ttctgattat  2400
caaccggggt acatatgatt gacatgctag ttttacgatt accgttcatc gattctcttg  2460
tttgctccag actctcaggc aatgacctga tagcctttgt agagacctct caaaaatagc  2520
taccctctcc ggcatgaatt tatcagctag aacggttgaa tatcatattg atggtgattt  2580
gactgtctcc ggcctttctc acccgtttga atctttacct acacattact caggcattgc  2640
atttaaaata tatgagggtt ctaaaaattt ttatccttgc gttgaaataa aggcttctcc  2700
cgcaaaagta ttacagggtc ataatgtttt tggtacaacc gatttagctt tatgctctga  2760
ggctttattg cttaattttg ccttgcctgt tatgatttat tggatgttgg  2820
aattcctgat gcggtatttt ctccttacgc atctgtgcgg tatttcacac cgcatatggt  2880
gcactctcag tacaatctgc tctgatgccg catagttaag ccagccccga cacccgccaa  2940
cacccgctga cgcgccctga cgggcttgtc tgctcccggc atccgcttac agacaagctg  3000
tgaccgtctc cgggagctgc atgtgtcaga ggttttcacc gtcatcaccg aaacgcgcga  3060
gacgaaaggg cctcgtgata cgcctatttt tataggttaa tgtcatgata ataatggttt  3120
cttagacgtc aggtggcact tttcggggaa atgtgcgcgg aacccctatt tgtttatttt  3180
tctaaataca ttcaaatatg tatccgctca tgagacaata accctgataa atgcttcaat  3240
aatattgaaa aaggaagagt atgagtattc aacatttccg tgtcgccctt attccctttt  3300
ttgcggcatt ttgccttcct gttttttgctc acccagaaaa gctggtgaaa gtaaaagatg  3360
ctgaagatca gttgggtgca cgagtgggtt acatcgaact ggatctcaac agcggtaaga  3420
tccttgagag ttttcgcccc gaagaacgtt ttccaatgat gagcactttt aaagttctgc  3480
tatgtggcgc ggtattatcc gtattgacg ccgggcaaga gcaactcggt cgccgcatac  3540
actattctca gaatgacttg gttgagtact caccagtcac agaaaagcat cttacggatg  3600
gcatgacagt aagagaatta tgcagtgctg ccataaccat gagtgataac actgcggcca  3660
acttacttct gacaacgatc ggaggaccga aggagctaac cgcttttttg cacaacatgg  3720
gggatcatgt aactcgcctt gatcgttggg aaccggagct gaatgaagcc ataccaaacg  3780
acgagcgtga caccacgatg cctgtagcaa tggcaacaac gttgcgcaaa ctattaactg  3840
gcgaactact tactctagct tcccggcaac aattaataga ctggatggag gcggataaag  3900
ttgcaggacc acttctgcgc tcggcccttc cggctggctg gtttattgct gataaatctg  3960
gagccggtga gcgtgggtct cgcggtatca ttgcagcact ggggccagat ggtaagccct  4020
cccgtatcgt agttatctac acgacgggga gtcaggcaac tatggatgaa cgaaatagac  4080
agatcgctga gataggtgcc tcactgatta agcattggta actgtcagac caagtttact  4140
catatatact ttagattgat ttaaaacttc attttttaatt taaaaggatc taggtgaaga  4200
tcctttttga taatctcatg accaaaatcc cttaacgtga gttttcgttc cactgagcgt  4260
cagaccccgt agaaaagatc aaaggatctt cttgagatcc tttttttctg cgcgtaatct  4320
gctgcttgca aacaaaaaaa ccaccgctac cagcggtggt ttgtttgccg gatcaagagc  4380
taccaactct ttttccgaag gtaactggct tcagcagagc gcagatacca aatactgtcc  4440
ttctagtgta gccgtagtta ggccaccact tcaagaactc tgtagcaccg cctacatacc  4500
tcgctctgct aatcctgtta ccagtggctg ctgccagtgg cgataagtcg tgtcttaccg  4560
ggttggactc aagacgatag ttaccggata aggcgcagcg gtcgggctga acggggggtt  4620
cgtgcacaca gcccagcttg gagcgaacga cctacaccga actgagatac ctacagcgtg  4680
agctatgaga aagcgccacg cttcccgaag ggagaaaggc ggacaggtat ccggtaagcg  4740
gcagggtcgg aacaggagag cgcacgaggg agcttccagg gggaaacgcc tggtatcttt  4800
atagtcctgt cgggtttcgc cacctctgac ttgagcgtcg atttttgtga tgctcgtcag  4860
gggggcggag cctatggaaa aacgccagca acgcggcctt tttacggttc ctggccttt  4920
gctggccttt tgctcacatg ttctttcctg cgttatcccc tgattctgtg gataaccgta  4980
```

-continued

```
ttaccgcctt tgagtgagct gataccgctc gccgcagccg aacgaccgag cgcagcgagt 5040
cagtgagcga ggaagcggaa gagcgcccaa tacgcaaacc gcctctcccc gcgcgttggc 5100
cgattcatta atgcagctgc gcgctcgctc gctcactgag gccgcccggg caaagcccgg 5160
gcgtcgggcg acctttggtc gcccggcctc agtgagcgag cgagcgcgca gagagggagt 5220
ggccaactcc atcactaggg gttccttgta gttaatgatt aacccgccat gctacttatc 5280
tacgtagcca tgctctagga cattgattat tgactagtgg agttccgcgt tacataactt 5340
acggtaaatg gcccgcctgg ctgaccgccc aacgaccccc gcccattgac gtcaataatg 5400
acgtatgttc ccatagtaac gccaataggg actttccatt gacgtcaatg ggtggagtat 5460
ttacggtaaa ctgcccactt ggcagtacat caagtgtatc atatgccaag tacgccccct 5520
attgacgtca atgacggtaa atggcccgcc tggcattatg cccagtacat gaccttatgg 5580
gactttccta cttggcagta catctacgta ttagtcatcg ctattaccat ggtcgaggtg 5640
agccccacgt tctgcttcac tctccccatc tccccccct cccaccccc aattttgtat 5700
ttatttattt tttaattatt ttgtgcagcg atggggcgg gggggggg gggcgcgc 5760
caggcgggc gggcggggc gagggcggg gcggggcgag gcggagaggt gcggcggcag 5820
ccaatcagag cggcgcgctc cgaaagtttc cttttatggc gaggcggcgg cggcggcggc 5880
cctataaaaa gcgaagcgcg cggcgggcgg gagtcgctgc gcgctgcctt cgccccgtgc 5940
cccgctccgc cgccgcctcg cgccgcccgc cccggctctg actgaccgcg ttactaaaac 6000
aggtaagtcc ggcctccgcg ccgggttttg gcgcctcccg cgggcgcccc cctcctcacg 6060
gcgagcgctg ccacgtcaga cgaagggcgc agcgagcgtc ctgatccttc cgcccggacg 6120
ctcaggacag cggcccgctg ctcataagac tcggccttag aacccagta tcagcagaag 6180
gacattttag gacgggactt gggtgactct agggcactgg ttttctttcc agagagcgga 6240
acaggcgagg aaaagtagtc ccttctcggc gattctgcgg agggatctcc gtggggcggt 6300
gaacgccgat gatgcctcta ctaaccatgt tcatgttttc tttttttttc tacaggtcct 6360
gggtgacgaa cagggtacc 6379
```